(12) United States Patent
Glaesner et al.

(10) Patent No.: US 8,183,340 B2
(45) Date of Patent: May 22, 2012

(54) GLP-1 PEGYLATED COMPOUNDS

(75) Inventors: Wolfgang Glaesner, Carmel, IN (US); John Philip Mayer, Indianapolis, IN (US); Rohn Lee Millican, Jr., Indianapolis, IN (US); Andrew Mark Vick, Fishers, IN (US); Lianshan Zhang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 509 days.

(21) Appl. No.: 11/913,365

(22) PCT Filed: May 11, 2006

(86) PCT No.: PCT/US2006/018284
§ 371 (c)(1),
(2), (4) Date: Nov. 1, 2007

(87) PCT Pub. No.: WO2006/124529
PCT Pub. Date: Nov. 23, 2006

(65) Prior Publication Data
US 2009/0215981 A1    Aug. 27, 2009

Related U.S. Application Data

(60) Provisional application No. 60/680,688, filed on May 13, 2005.

(51) Int. Cl.
*A61K 38/26* (2006.01)
*C07K 14/605* (2006.01)
*A61P 3/10* (2006.01)

(52) U.S. Cl. .......... 530/308; 530/324; 514/7.2; 514/6.8; 514/6.9; 514/4.8; 514/11.7

(58) Field of Classification Search ................ None
See application file for complete search history.

(56) References Cited

U.S. PATENT DOCUMENTS

| | | | |
|---|---|---|---|
| 4,179,337 A * | 12/1979 | Davis et al. | 435/181 |
| 4,343,898 A | 8/1982 | Markussen | |
| 5,120,712 A | 6/1992 | Habener | |
| 5,445,090 A | 8/1995 | Conley, Jr. | |
| 5,900,461 A | 5/1999 | Harris | |
| 5,932,462 A | 8/1999 | Harris et al. | |
| 6,006,753 A | 12/1999 | Efendic | |
| 6,436,386 B1 | 8/2002 | Roberts et al. | |
| 6,437,025 B1 | 8/2002 | Harris et al. | |
| 6,448,369 B1 | 9/2002 | Bentley et al. | |
| 6,495,659 B2 | 12/2002 | Bentley et al. | |
| 6,514,491 B1 | 2/2003 | Bentley et al. | |
| 6,515,100 B2 | 2/2003 | Harris | |
| 7,557,183 B2 * | 7/2009 | DiMarchi et al. | 530/308 |

FOREIGN PATENT DOCUMENTS

| WO | WO 98/08531 | 3/1998 |
|---|---|---|
| WO | WO 98/19698 | 5/1998 |
| WO | WO 99/64060 | 12/1999 |
| WO | WO 00/07617 | 2/2000 |
| WO | WO 00/16797 | 3/2000 |
| WO | 2004/093823 | 11/2004 |

OTHER PUBLICATIONS

Lu, Y. and Felix, A. "Pegylated Peptides II Solid-phase synthesis of amino-, carboxy- and side-chain pegylated peptides." Int. J. Peptide Protein Rev, vol. 43, 1994, pp. 127-138.
Roberts, M., et al. "Chemistry for peptide and protein PEGylation." Advanced Drug Delivery Reviews, vol. 54, 2002, pp. 459-476.
Zalipsky, S. "Functionalized Poly(ethylene glycol) for Preparation of Biologically Relevant Conjugates." Bioconjugate Chem. vol. 6, 1995, pp. 150-165.

* cited by examiner

*Primary Examiner* — Daniel C Gamett
(74) *Attorney, Agent, or Firm* — Andrea M. Castetter; Gregory A. Cox

(57) ABSTRACT

The invention provides GLP-1 compounds coupled to two polyethylene glycol molecule or derivative thereof, resulting in a biologically active peptide with an extended half-life and a slower clearance when compared to that of unPEGylated peptide. These PEGylated GLP-1 compounds and compositions are useful in treating conditions or disorders benefited by lowering blood glucose, decreasing food intake, decreasing gastric or intestinal emptying, increasing beta (β) cell population, or decreasing gastric or intestinal motility.

4 Claims, No Drawings

```
                          SEQUENCE LISTING

<160> NUMBER OF SEQ ID NOS: 1

<210> SEQ ID NO 1
<211> LENGTH: 40
<212> TYPE: PRT
<213> ORGANISM: Artificial
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr
<220> FEATURE:
<221> NAME/KEY: MISC_FEATURE
<222> LOCATION: (2)..(2)
<223> OTHER INFORMATION: Ala is D-isomer
<220> FEATURE:
<221> NAME/KEY: MISC_FEATURE
<222> LOCATION: (16)..(16)
<223> OTHER INFORMATION: Xaa at position 16 is Gly, Glue, Asp, or Lys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (40)..(40)
<223> OTHER INFORMATION: Xaa at position 40 is Cys or Cys-NH2

<400> SEQUENCE: 1

His Xaa Glu Gly Thr Phe Thr Ser Asp Val Ser Ser Tyr Leu Glu Xaa
1               5                  10                  15

Gln Ala Ala Lys Glu Phe Ile Ala Trp Leu Xaa Lys Gly Gly Pro Ser
            20                  25                  30

Ser Gly Ala Pro Pro Pro Cys Xaa
        35                  40
```

GLP-1 PEGYLATED COMPOUNDS

This is the national phase application, under 35 USC 371, for PCT/US2006/018284, filed 11 May 2006, which claims the priority of U.S. provisional application No. 60/680,688, filed 13 May 2005.

FIELD OF THE INVENTION

The present invention relates to polyethylene glycol (PEG) modified glucagon-like peptide-1 (GLP-1) compounds and related compositions and methods useful in treating conditions or disorders benefited by lowering blood glucose, decreasing food intake, decreasing gastric or intestinal emptying, increasing beta (β) cell number and/or function and/or inhibiting β cell apoptosis, or decreasing gastric or intestinal motility.

BACKGROUND OF THE INVENTION

GLP-1 induces numerous biological effects such as stimulating insulin secretion, inhibiting glucagon secretion, inhibiting gastric emptying, inhibiting gastric motility or intestinal motility, enhancing glucose utilization, and inducing weight loss. GLP-1 may further act to prevent the pancreatic β-cell deterioration that occurs as non-insulin dependent diabetes mellitus (NIDDM) progresses. A significant characteristic of GLP-1 is its ability to stimulate insulin secretion without the associated risk of hypoglycemia. GLP-1 induces insulin secretion only when glucose levels are elevated unlike other therapies that act by increasing insulin expression regardless of whether glucose levels are elevated.

The usefulness of therapy involving GLP-1 peptides has been limited by the fact that GLP-1(1-37) is poorly active, and the two naturally occurring truncated peptides, GLP-1(7-37) OH and GLP-1(7-36)$NH_2$, are rapidly cleared in vivo and have extremely short in vivo half lives. It is known that endogenously produced dipeptidyl-peptidase IV (DPP-IV) inactivates circulating GLP-1 peptides by removing the N-terminal histidine and alanine residues and is a major reason for the short in vivo half-life.

While various approaches have resulted in GLP-1 compounds with a longer half-life or greater potency than that of native GLP-1, additional compounds are needed to further decrease clearance and increase half-life thereby optimizing GLP-1's ability to be useful as a therapeutic that can be administered a minimum number of times during a prolonged period of time. International Application Nos. PCT/US2004/006082 and PCT/US2000/11814 describe covalent attachment of one or more molecules of PEG to various GLP-1 and exendin compounds. These compounds may have a half-life in excess of 24 hours allowing for fewer administrations of the PEGylated GLP-1 compound while maintaining a high blood level of the compound over a prolonged period of time.

Further research has elucidated a problem wherein the separation of PEG from a PEGylated GLP-1 or exendin compound occurs during prolonged shelf storage. As a result, the free GLP-1 or exendin peptide increases the initial peak concentration exposure profile through the therapeutic window. This has the possibility of increasing the side effects of nausea and vomiting.

The present invention seeks to overcome the problems associated with the prolonged shelf storage and the potential of separation of PEG from the PEGylated GLP-1 or exendin compound by introducing two PEGylation sites into a GLP-1 or exendin compound and then PEGylating those two PEGylation sites simultaneously. The advantages of this approach are at least four-fold. First, PEGylation of the compounds will dramatically improve the in vivo half-lives of the compounds. Second, PEGylation of the compounds will slow down the absorption rate of the compound and thus, reduce initial burst of the drug that is believed to be responsible for the side effects. Third, linear PEGs can be used directly for PEGylation and will simplify the synthesis procedure. Fourth, tandem PEGylation will alleviate the issues associated with prolonged shelf storage and the potential of separation of PEG from the PEGylated GLP-1 or exendin compound by decreasing the probability that both PEGs will be separated from the same GLP-1 or exendin peptide molecule.

Additionally, introducing two PEGylation sites into a GLP-1 or exendin compound at the C-terminal end of the compound and then PEGylating those two PEGylation sites simultaneously resulted in PEGylated compounds having greater activity over those PEGylated compounds wherein at least one of the PEGylation sites is not at the C-terminal end of the peptide. Further, attaching a linker comprising two PEGylation sites at the C-terminal end of a GLP-1 compound and then PEGylating those two PEGylation sites simultaneously resulted in PEGylated GLP-1 compounds having greater activity over those PEGylated compounds wherein the PEGylation sites are attached at the C-terminal end of a GLP-1 compound without a linker.

Such PEGylated GLP-1 compounds may be used therapeutically to treat subjects with disorders including, but not limited to, diabetes, obesity, gastric and/or intestinal motility abnormalities, beta (β) cell deficiency (e.g. insufficient or nonfunctioning β cells), and gastric and/or intestinal emptying abnormalities with a particular advantage being that the PEGylated GLP-1 compounds of the invention require fewer doses during a 24 hour period, increasing both the convenience to a subject in need of such therapy and the likelihood of subject's compliance with dosing requirements.

SUMMARY OF THE INVENTION

The invention described herein provides GLP-1 compounds covalently attached to two molecules of polyethylene glycol (PEG), or a derivative thereof wherein each PEG is attached at a cysteine residue, resulting in PEGylated GLP-1 compounds with an elimination half-life of at least one hour, or at least 3, 5, 7, 10, 15, 20 hours or at least 24 hours. The PEGylated GLP-1 compounds of the present invention have a clearance value of 200 ml/h/kg or less, or 180, 150, 120, 100, 80, 60 ml/h/kg or less, or less than 50, 40 or 20 ml/h/kg.

PEGylated GLP-1 compounds of the present invention comprises an amino acid sequence of the formula:

Formula I
(SEQ ID NO: 1)
His-Xaa$_8$-Glu-Gly-Thr-Phe-Thr-Ser-Asp-Val-Ser-Ser-

Tyr-Leu-Glu-Xaa$_{22}$-Gln-Ala-Ala-Lys-Glu-Phe-Ile-Ala-

Trp-Leu-Xaa$_{33}$-Lys-Gly-Gly-Pro-Ser-Ser-Gly-Ala-Pro-

Pro-Pro-Cys$_{45}$-Xaa$_{46}$ wherein Xaa$_8$ is: D-Ala, Gly, Val, Leu, Ile, Ser, or Thr;
Xaa$_{22}$ is: Gly, Glu, Asp, or Lys;
Xaa$_{33}$ is: Val or Ile
Xaa$_{46}$ is: Cys or Cys-$NH_2$
and wherein one PEG molecule is covalently attached to Cys$_{45}$ and one PEG molecule is covalently attached to Cys$_{46}$ or Cys$_{46}$-$NH_2$.

Preferably, for the PEGylated GLP-1 compounds of Formula I: $Xaa_8$ is Gly or Val; $Xaa_{22}$ is Gly or Glu; $Xaa_{33}$ is Val or Ile; and $Xaa_{46}$ is Cys or Cys-$NH_2$. Also preferable are the PEGylated GLP-1 compounds of Formula I, wherein $Xaa_8$ is Val; $Xaa_{22}$ is Glu; $Xaa_{33}$ is Val or Ile; and $Xaa_{46}$ is Cys or Cys-$NH_2$. Also preferable are the PEGylated GLP-1 compounds of Formula I, wherein $Xaa_8$ is Val; $Xaa_{22}$ is Glu; $Xaa_{33}$ is Val; and $Xaa_{46}$ is Cys. Also preferable are the PEGylated GLP-1 compounds of Formula I, wherein $Xaa_8$ is Val; $Xaa_{22}$ is Glu; $Xaa_{33}$ is Val; and $Xaa_{46}$ is Cys-$NH_2$. Also preferable are the PEGylated GLP-1 compounds of Formula I, wherein $Xaa_8$ is Val; $Xaa_{22}$ is Glu; $Xaa_{33}$ is Ile; and $Xaa_{46}$ is Cys. Also preferable are the PEGylated GLP-1 compounds of Formula I, wherein $Xaa_8$ is Val; $Xaa_{22}$ is Glu; $Xaa_{33}$ is Ile; and $Xaa_{46}$ is Cys-$NH_2$.

The polyethylene glycol ("PEG") polymers used in the invention have molecular weights between 500 and 100,000 daltons, or between 5,000 and 40,000 daltons, or between 20,000 and 60,000 daltons, or between 20,000 and 40,000 daltons, and may be linear or branched molecules, and may be polyethylene glycol derivatives as described in the art. The PEG molecule covalently attached to GLP-1 compounds in the present invention is not intended to be limited to a particular type. Preferably the PEG is a 20 kilodalton linear methoxy PEG maleimide. More preferably the PEG is:

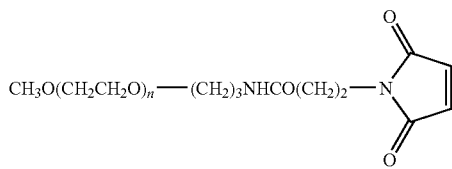

The present invention encompasses a method of stimulating the GLP-1 receptor in a subject in need of such stimulation, said method comprising the step of administering to the subject an effective amount of a PEGylated GLP-1 compound described herein. Subjects in need of GLP-1 receptor stimulation include those with non-insulin dependent diabetes, stress-induced hyperglycemia, obesity, gastric and/or intestinal motility or emptying disorders including, for example, irritable bowel syndrome, beta (β) cell deficiency, and functional dyspepsia.

DETAILED DESCRIPTION OF THE INVENTION

Glucagon-Like Peptide 1 (GLP-1) is a 37 amino acid peptide secreted by the L-cells of the intestine in response to food ingestion. Numerous GLP-1 analogs and derivatives have been described in the art. The present invention describes modifications to GLP-1 compounds that result in extended elimination half-life and/or reduced clearance. Incorporation of cysteine residues into particular amino acid sites of the peptide provides a thiol group to which a polyethylene glycol (PEG) or PEG derivative may be covalently attached resulting in a PEGylated GLP-1 compound.

The term "GLP-1 compound" as used herein, includes native GLP-1, [GLP-1(7-37)OH or GLP-1(7-36)$NH_2$], GLP-1 analogs, GLP-1 derivatives, GLP-1 biologically active fragments, extended GLP-1 or an analog or fragment of an extended GLP-1 peptide, exendin-4 analogs and exendin-4 derivatives. Preferably, a GLP-1 analog has the amino acid sequence of GLP-1(7-37)OH or an extended GLP-1 peptide so that 1, 2, 3, 4, 5 or 6 amino acids differ from the amino acid in the corresponding position of GLP-1(7-37)OH or a fragment of GLP-1(7-37)OH or modified so that 0, 1, 2, 3, 4, 5 or 6 amino acids differ from the amino acid in the corresponding position of an extended GLP-1 peptide.

The term "PEGylated" when referring to a GLP-1 compound of the present invention refers to a GLP-1 compound that is chemically modified by covalent attachment of two molecules of polyethylene glycol or a derivative thereof. Furthermore, it is intended that the term "PEG" refers to polyethylene glycol or a derivative thereof as are known in the art (see, e.g., U.S. Pat. Nos. 5,445,090; 5,900,461; 5,932,462; 6,436,386; 6,448,369; 6,437,025; 6,448,369; 6,495,659; 6,515,100 and 6,514,491). Preferably, in PEGylated GLP-1 compounds of the present invention, PEG (or a derivative thereof) is covalently attached to two introduced cysteine residues in the GLP-1 compound. Preferably, the two introduced cysteine residues in the GLP-1 compound are at position 45 and 46.

"Insulinotropic activity" refers to the ability to stimulate insulin secretion in response to elevated glucose levels, thereby causing glucose uptake by cells and decreased plasma glucose levels. Insulinotropic activity can be assessed by methods known in the art, including using in vivo experiments and in vitro assays that measure GLP-1 receptor binding activity or receptor activation, e.g., assays employing pancreatic islet cells or insulinoma cells, as described in EP 619,322 to Gelfand, et al., and U.S. Pat. No. 5,120,712, respectively. Insulinotropic activity is routinely measured in humans by measuring insulin levels or C-peptide levels. For the purposes of the present invention an in vitro GLP-1 receptor signaling assay is used to determine whether a PEGylated GLP-1 compound of the present invention will exhibit insulinotropic activity in vivo. Insulinotropic activity is an activity that may be used to demonstrate that the PEGylated GLP-1 compound is biologically active. All exemplified PEGylated GLP-1 compounds of the invention have insulinotropic activity (See Example 6).

"In vitro potency" as used herein, is the measure of the ability of a peptide to activate the GLP-1 receptor in a cell-based assay. In vitro potency is expressed as the "$EC_{50}$" which is the effective concentration of compound that results in 50% activity in a single dose-response experiment. For the purposes of the present invention, in vitro potency is determined using a fluorescence assay that employs HEK-293 cells that stably express the human GLP-1 receptor. These HEK-293 cells have stably integrated a DNA vector having a cAMP response element (CRE) driving expression of the luciferase gene. The interaction of a GLP-1 compound or a PEGylated GLP-1 compound with the receptor initiates a signal that results in activation of the cAMP response element and subsequent expression of luciferase. The $EC_{50}$ values for the PEGylated GLP-1 compounds listed in Example 3 were determined using the luciferase assay described above. Relative in vitro potency values may be established by running $Val_8$-GLP-1(7-37)OH or native GLP-1 as a control and assigning the control a reference value of 100%.

The term "plasma half-life" refers to the time in which half of the relevant molecules circulate in the plasma prior to being cleared. An alternatively used term is "elimination half-life." The term "extended" or "longer" used in the context of plasma half-life or elimination half-life indicates there is a statistically significant increase in the half-life of a PEGylated GLP-1 compound relative to that of the reference molecule (e.g., the non-PEGylated form of the peptide or the native peptide) as determined under comparable conditions. Preferably a PEGylated GLP-1 compound of the present invention has an elimination half-life of at least one hour, more preferably at least 3, 5, 7, 10, 15, 20 hours and most preferably at least 24 hours. The half-life reported herein in Examples 4 and 5 are the elimination half-life; it is that which corresponds to the terminal log-linear rate of elimination. Those of skill in the art appreciate that half-life is a derived parameter that changes as a function of both clearance and volume of distribution.

Clearance is the measure of the body's ability to eliminate a drug. As clearance decreases due, for example, to modifications to a drug, half-life would be expected to increase. However, this reciprocal relationship is exact only when there is no change in the volume of distribution. A useful approximate relationship between the terminal log-linear half-life ($t_{1/2}$), clearance (C), and volume of distribution (V) is given by the equation: $t_{1/2} \approx 0.693$ (V/C). Clearance does not indicate how much drug is being removed but, rather, the volume of biological fluid such as blood or plasma that would have to be completely freed of drug to account for the elimination. Clearance is expressed as a volume per unit of time. The PEGylated GLP-1 compounds of the present invention have a clearance value of 200 ml/h/kg or less, or 180, 150, 120, 100, 80, 60 ml/h/kg or less, or 50, 40 or 20 m/l/kg or less (See Example 4 and 5).

In the present invention, a Cys amino acid is incorporated at positions 45 and 46 of the GLP-1 compounds. The resulting molecule is PEGylated at the Cys amino acids resulting in a modified molecule that retains all or a portion of biological activity while having a longer half-life than that of the unmodified molecule or than that of a native molecule.

The GLP-1 compounds for use in the present invention can be prepared by using standard methods of solution phase or solid-phase peptide synthesis techniques.

Once a GLP-1 compound is prepared and purified, it is PEGylated by covalently linking two PEG molecules to the GLP-1 compound. A wide variety of methods have been described in the art to covalently conjugate PEGs to peptides (for review article see, Roberts, M. et al. *Advanced Drug Delivery Reviews*, 54:459-476, 2002). PEGylation of peptides at the carboxy-terminus may be performed via enzymatic coupling using recombinant GLP-1 peptide as a precursor or alternative methods known in the art and described. See e.g. U.S. Pat. No. 4,343,898 or *International Journal of Peptide & Protein Research*. 43: 127-38, 1994. One method for preparing the PEGylated GLP-1 compounds of the present invention involves the use of PEG-maleimide to directly attach PEG to a thiol group of the peptide. The introduction of a thiol functionality can be achieved by adding or inserting a Cys residue onto or into the peptide at positions described above. A thiol functionality can also be introduced onto the side-chain of the peptide (e.g. acylation of lysine ε-amino group of a thiol-containing acid). A PEGylation process of the present invention utilizes Michael addition to form a stable thioether linker. The reaction is highly specific and takes place under mild conditions in the presence of other functional groups. PEG maleimide has been used as a reactive polymer for preparing well-defined, bioactive PEG-protein conjugates. It is preferable that the procedure uses a molar excess of a thiol-containing GLP-1 compound relative to PEG maleimide to drive the reaction to completion. The reactions are preferably performed between pH 4.0 and 9.0 at room temperature for 1 to 40 hours. The excess of unPEGylated thiol-containing peptide is readily separated from the PEGylated product by conventional separation methods. Exemplary conditions required for PEGylation of GLP-1 compounds are set forth in Example 1 and 2. Cysteine PEGylation may be performed using PEG maleimide or bifurcated PEG maleimide. A preferred PEG is a 20 kilodalton linear methoxy PEG maleimide.

In its typical form, PEG is a linear polymer with terminal hydroxyl groups and has the formula HO—CH$_2$CH$_2$—(CH$_2$CH$_2$O)n-CH$_2$CH$_2$—OH, where n is from about 8 to about 4000. The terminal hydrogen may be substituted with a protective group such as an alkyl or aryl group. Preferably, PEG has at least one hydroxy group, more preferably it is a terminal hydroxy group. It is this hydroxy group which is preferably activated to react with the peptide. There are many forms of PEG useful for the present invention. Numerous derivatives of PEG exist in the art and are suitable for use in the invention. (See, e.g., U.S. Pat. Nos. 5,445,090; 5,900,461; 5,932,462; 6,436,386; 6,448,369; 6,437,025; 6,448,369; 6,495,659; 6,515,100 and 6,514,491 and Zalipsky, S. *Bioconjugate Chem.* 6:150-165, 1995). The PEG molecule covalently attached to GLP-1 compounds in the present invention is not intended to be limited to a particular type. PEG's molecular weight is preferably from 500-100,000 daltons and more preferably from 20,000-60,000 daltons and most preferably from 20,000-40,000 daltons. PEG may be linear or branched.

PEGylated GLP-1 compounds of the present invention have an in vitro biological activity that is at least 0.5% that of native GLP-1 or of Val$_8$-GLP-1(7-37)OH. PEGylated GLP-1 compounds of the present invention have an in vitro biological activity that is at least 1% that of native GLP-1 or of Val$_8$-GLP-1(7-37)OH. PEGylated GLP-1 compounds of the present invention have an in vitro biological activity that is at least 3% that of native GLP-1 or of Val$_8$-GLP-1(7-37)OH. Such biological activity may be determined by the in vitro potency assay as described herein (Example 3) or by other GLP-1 assays known in the art. Although some PEGylated GLP-1 compounds of the invention may have biological activity lower than that of native GLP-1 or of Val$_8$-GLP-1(7-37)OH as measured in a particular assay; this activity decrease is compensated by the compound's extended half-life and/or lower clearance value.

Administration of the PEGylated GLP-1 compounds may be via any route known to be effective by the physician of ordinary skill. Peripheral parenteral is one such method. Parenteral administration is commonly understood in the medical literature as the injection of a dosage form into the body by a sterile syringe or some other mechanical device such as an infusion pump. Peripheral parenteral routes can include intravenous, intramuscular, subcutaneous, and intraperitoneal routes of administration. The PEGylated GLP-1 compounds of the present invention may also be amenable to administration by oral, rectal, nasal, or lower respiratory routes, which are non-parenteral routes. Of these non-parenteral routes, the lower respiratory route and the oral route are preferred.

The PEGylated GLP-1 compounds of the present invention can be used to treat a wide variety of diseases and conditions. The PEGylated GLP-1 compounds of the present invention primarily exert their biological effects by acting at a receptor referred to as the "GLP-1 receptor." Subjects with diseases and/or conditions that respond favorably to GLP-1 receptor stimulation or to the administration of GLP-1 compounds can therefore be treated with the PEGylated GLP-1 compounds of the present invention. These subjects are said to "be in need of treatment with GLP-1 compounds" or "in need of GLP-1 receptor stimulation". Included are subjects with non-insulin dependent diabetes, insulin dependent diabetes, stroke (see WO 00/16797), myocardial infarction (see WO 98/08531), obesity (see WO 98/19698), catabolic changes after surgery (see U.S. Pat. No. 6,006,753), functional dyspepsia and irritable bowel syndrome (see WO 99/64060). Also included are subjects requiring prophylactic treatment with a GLP-1 compound, e.g., subjects at risk for developing non-insulin dependent diabetes (see WO 00/07617). Subjects with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

An effective amount of the PEGylated GLP-1 compounds described herein is the quantity which results in a desired therapeutic and/or prophylactic effect without causing unacceptable side-effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a PEGylated GLP-1 compound for the treatment of diabetes is the quantity that would result in greater control of blood glucose concentration than in the absence of treatment, thereby resulting in a delay in the onset of diabetic complications such as retinopathy, neuropathy or kidney disease. An "effective amount" of a PEGylated GLP-1 compound for the prevention of diabetes is the quantity that would delay, compared with the absence of treatment, the onset of elevated blood glucose levels that require treatment with anti-hyperglycaemic drugs such as sulfonyl ureas, thiazolidinediones, metformin, insulin and/or bisguanidines. Typically, the PEGylated GLP-1 compounds of the present invention will be administered such that plasma levels are within the range of about 5 picomoles/liter and about 200 picomoles/liter. Optimum plasma levels for $Val_8$-GLP-1(7-37)OH were determined to be between 30 picomoles/liter and about 200 picomoles/liter.

The dose of a PEGylated GLP-1 compound effective to normalize a patient's blood glucose will depend on a number of factors, among which are included, without limitation, the subject's sex, weight and age, the severity of inability to regulate blood glucose, the route of administration and bioavailability, the pharmacokinetic profile of the PEGylated GLP-1 compound, the potency, and the formulation. A typical dose range for the PEGylated GLP-1 compounds of the present invention will range from about 0.01 mg per day to about 1000 mg per day for an adult. Preferably, the dosage ranges from about 0.1 mg per day to about 100 mg per day, more preferably from about 1.0 mg/day to about 10 mg/day.

It is preferable that the PEGylated GLP-1 compounds of the present invention be administered either once every two weeks or once a week. Depending on the disease being treated, it may be necessary to administer the PEGylated GLP-1 compounds more frequently such as two to three time per week.

A "subject" is a mammal, preferably a human, but can also be an animal, e.g., companion animals (e.g., dogs, cats, and the like), farm animals (e.g., cows, sheep, pigs, horses, and the like) and laboratory animals (e.g., rats, mice, guinea pigs, and the like).

The peptides used to generate the PEGylated GLP-1 compounds of the present invention can be prepared by using standard methods of solution phase or solid-phase peptide synthesis techniques.

The invention is illustrated by the following examples that are not intended to be limiting in any way.

EXAMPLES

Example 1

PEGylation of GLP-1 Related Analogs

PEGylation reactions are run under conditions that permit the formation of a thioether bond. Specifically, the pH of the solution ranges from about 4 to 9 and the thiol-containing peptide concentrations range from 1 to 10 molar excess of methoxy-PEG2-MAL concentration. The PEGylation reactions are normally run at room temperature. The PEGylated GLP-1 peptide is then isolated using reverse-phase HPLC ion exchange chromatography, or size exclusion chromatography (SEC). PEGylated GLP-1 analogues are characterized using analytical RP-HPLC, HPLC-SEC, SDS-PAGE, and/or MALDI Mass Spectrometry.

Thiol-containing GLP-1 peptides are reacted with polyethylene glycol-maleimide (PEG-maleimide) to produce derivatives with PEG covalently attached via a thioether bond. For example, a GLP-1 compound, 46aa in length; 7.5 mg, 1.8 μmol is dissolved in 2 ml of 200 mM phosphate buffer containing 20 mM EDTA, pH 7.4. The solution is then purged with argon. To this solution is added 40 mg of methoxy-PEG-MAL, a linear or bifurcated PEG maleimide (Shearwater Polymers, Inc., Huntsville, Ala.) (0.55:1 mole/mole ratio of PEG to peptide). The reaction is performed for 2 hours. Then 25 mg of the PEGylated peptide is purified by RP-HPLC, characterized by size-exclusion HPLC, and tested for in vitro activity.

Example 2

2×20 kDa-PEG-Maleimide Reaction with GLP Analogs

GLP-1 analogs are selectively PEGylated at the introduced cysteine residues using maleimide-activated linear 20 kDa mPEG (NOF, Inc.). For the PEGylation reaction, the peptide to be PEGylated is dissolved in 100 mM NH4Ac buffer containing 10 mM EDTA at pH 6.8 and a 1.25-fold molar excess of bulk 20 kDa-mPEG is added. The reaction is allowed to stir at room temperature for 1-4 hours and SP-Sepharose cation exchange chromatography is used to separate PEGylated compound from free PEG and free peptide. The conjugate is desalted by RP-HPLC and lyophilized.

Example 3

In Vitro Activity Assay

HEK-293 cells stably expressing the human GLP-1 receptor, using a CRE-Luciferase system, are seeded at 30,000 cells/well/80 μl low serum DMEM F12 medium into 96 well plates. The day after seeding, 20 μl aliquots of test protein dissolved in 0.5% BSA are mixed and incubated with the cells for 5 hours. Generally 10 dilutions containing from 0.001 nM to 10 nM are prepared for the test GLP-1 compounds and 0.0003 nM and 3 nM are prepared for the $Val_8$-GLP-1(7-37) OH standard before addition to the cells to generate a dose response curve from which $EC_{50}$ values are determined. After incubation, 100 μl of Luciferase reagent is added directly to each plate and mixed gently for 2 minutes. Plates are placed in a Tri-lux luminometer and light output resulting from luciferase expression is calculated. The average $EC_{50}$ value for PEGylated GLP-1 compound of Formula I, wherein $Xaa_8$ is Val; $Xaa_{22}$ is Glu; $Xaa_{33}$ is Ile; and $Xaa_{46}$ is Cys is 0.22±0.03 nM. The average $EC_{50}$ value for PEGylated GLP-1 compound of Formula I, wherein $Xaa_8$ is Val; $Xaa_{22}$ is Glu; $Xaa_{33}$ is Ile; and $Xaa_{46}$ is Cys-NH$_2$ is 0.36±0.04 nM.

Example 4

Pharmacokinetic Analysis of Derivatized GLP-1 Peptide

A PEGylated GLP-1 compound of Formula I, wherein $Xaa_8$ is Val; $Xaa_{22}$ is Glu; $Xaa_{33}$ is Ile; and $Xaa_{46}$ is Cys-NH$_2$ is administered by intravenous (IV) or subcutaneous (SC) routes at a dose of 0.1 mg/kg to male SD rats. The animals (3 rats per group) are bled at various times between 0 and 192 hours after dosing. Plasma is collected from each sample and analyzed by N-terminal specific radioimmunoassay. Pharmacokinetic parameters are calculated using noncompartmental methods (WinNonlin Pro). By IV administration, the PEGylated GLP-1 analog has an elimination half-life of approximately 1.2 days while by SC administration the PEGylated GLP-1 analog has an elimination half-life of approximately 1.1 days. No adverse clinical observations are associated with IV or SC administration of 0.1 mg/kg. Prolonged elimination half-life, slow clearance and subcutaneous bioavailability (approximately 30%) are observed for the compound. Representative data are shown below in Table 1

TABLE 1

Mean (±SD) PK parameter values for a PEGylated GLP-1 compound of Formula I, wherein $Xaa_8$ is Val; $Xaa_{22}$ is Glu; $Xaa_{33}$ is Ile; and $Xaa_{46}$ is Cys-NH$_2$ following intravenous or subcutaneous administration of 0.1 mg/kg to male SD rats.

| Route | $C_{max}^a$ (ng/mL) | $T_{max}^b$ (h) | $AUC_{0-last}^c$ (ng * h/mL) | $t_{1/2}^d$ (h) | $CL/F^e$ (mL/h/kg) | $Vss/F^f$ (mL/kg) |
|---|---|---|---|---|---|---|
| IV | 2020 | 0.08 | 52292 | 25.8 | 1.9 | 54 |
|  | (235) | (0.00) | (4546) | (2.2) | (0.2) | (2.5) |
| SC | 191 | 24.0 | 15423 | 28.3 | 6.5 | 268 |
| (SD) | (31) | (0.0) | (2821) | (0.8) | (1.2) | (56) |

$^a$Maximum observed plasma concentration.
$^b$Time of maximum observed plasma concentration.
$^c$Area under the plasma concentration-time curve measured from 0 to last time point.
$^d$Elimination half-life.
$^e$Total body clearance as a function of bioavailability.
$^f$Steady state volume of distribution as a function of bioavailability.

When Val$_8$-GLP(7-37)OH is similarly IV administered to Fischer 344 rats at a dose of 10 μg/kg, profoundly different clearance and elimination half-life values are obtained as listed below.

| Clearance: | 1449 ml/hr/kg |
|---|---|
| t½ (hr): | 0.05 |

Example 5

Pharmacokenetic Analysis of Derivatized GLP-1 Peptide

A PEGylated GLP-1 compound of Formula I, wherein $Xaa_8$ is Val; $Xaa_{22}$ is Glu; $Xaa_{33}$ is Ile; and $Xaa_{46}$ is Cys-NH$_2$ is administered by subcutaneous (SC) route at a dose of 0.01 mg/kg to male cynomolgus monkeys. The animals are bled at various times between 0 and 168 hours after dosing. Serum is collected from each sample and analyzed by N-terminal specific radioimmunoassay. Pharmacokinetic parameters are calculated using noncompartmental methods (WinNonlin Pro). Representative data are shown below in Table 2.

TABLE 2

Mean (±SD) PK parameter values for a PEGylated GLP-1 compound of Formula I, wherein $Xaa_8$ is Val; $Xaa_{22}$ is Glu; $Xaa_{33}$ is Ile; and $Xaa_{46}$ is Cys-NH$_2$ following subcutaneous administration of 0.01 mg/kg to male cynomolgus monkeys.

| Animal # | $C_{max}^a$ (ng/mL) | $T_{max}^b$ (hr) | $AUC_{0-last}^c$ (ng * hr/mL) | $t_{1/2}^d$ (hr) | $CL/F^e$ (mL/hr/kg) | $V_{ss}/F^f$ (mL/kg) |
|---|---|---|---|---|---|---|
| Mean | 69.49 | 48 | 7464.78 | 75.69 | 1.06 | 117.15 |
| SD | 17.07 | 0 | 1612.03 | 11.67 | 0.26 | 44.89 |

Abbreviations:
SD = standard deviation
$^a$Maximum observed serum concentration.
$^b$Time of maximum observed serum concentration.
$^c$Area under the serum concentration-time curve measured from 0 to last time point.
$^d$Elimination half-life estimate.
$^e$Total body clearance as a function of bioavailability.
$^f$Steady state volume of distribution as a function of bioavailability.

Example 6

Pharmacodynamic Analysis of Derivatized GLP-1 Peptide

A PEGylated GLP-1 compound of Formula I, wherein $Xaa_8$ is Val; $Xaa_{22}$ is Glu; $Xaa_{33}$ is Ile; and $Xaa_{46}$ is Cys-NH$_2$ is administered by subcutaneous (SC) route at a dose of 0.01 mg/kg to male cynomolgus monkeys. A stepped intravenous glucose infusion is conducted immediately after SC administration of vehicle control (phosphate buffered saline) and 1, 5, and 7 days after SC administration of 0.01 mg/kg PEGylated GLP-1 analog. Stepped intravenous glucose infusion procedures are conducted in sedated monkeys after a 16-hour fast. Blood samples are drawn at 10 minutes prior to start of glucose infusion and immediately prior to start of glucose infusion to define baseline. A stepped infusion of glucose (20% dextrose) is then initiated at a rate of 10 mg/kg/min for 20 minutes followed by an infusion of 25 mg/kg/min for an additional 20 minutes. Blood samples are taken at 10-minute intervals throughout the infusion period. Insulin levels are determined by immunoassay. Insulinotropic activity is demonstrated for at least 7 days (relative to placebo; p<0.0001) following a single SC injection of 0.01 mg/kg the PEGylated GLP-1 analog. Representative data are shown below in Table 3.

TABLE 3

Mean (±SD) PD parameter values for a PEGylated GLP-1 compound of Formula I, wherein $Xaa_8$ is Val; $Xaa_{22}$ is Glu; $Xaa_{33}$ is Ile; and $Xaa_{46}$ is Cys-NH$_2$ following subcutaneous administration of 0.01 mg/kg to male cynomolgus monkeys.

| Insulin AUC Group | | AUClast (pM * min) |
|---|---|---|
| Vehicle | Mean | 14983 |
|  | SD | 5789 |
|  | SE | 2363 |
| Day 1 | Mean | 30862 |
|  | SD | 10770 |
|  | SE | 4397 |
| Day 5 | Mean | 27203 |
|  | SD | 6507 |
|  | SE | 2657 |
| Day 7 | Mean | 28542 |
|  | SD | 7685 |
|  | SE | 3137 |

We claim:

1. A di-PEGylated GLP-1 compound comprising amino acid sequence:

Formula I
(SEQ ID NO: 1)
His-Xaa$_8$-Glu-Gly-Thr-Phe-Thr-Ser-Asp-Val-Ser-Ser-

Tyr-Leu-Glu-Xaa$_{22}$-Gln-Ala-Ala-Lys-Glu-Phe-Ile-Ala-

Trp-Leu-Xaa$_{33}$-Lys-Gly-Gly-Pro-Ser-Ser-Gly-Ala-Pro-

Pro-Pro-Cys$_{45}$-Xaa$_{46}$ wherein Xaa$_8$ is Val, Xaa$_{22}$ is Glu, Xaa$_{33}$ is Ile, and Xaa$_{46}$ is Cys-NH$_2$ and wherein one PEG molecule is covalently attached to Cys$_{45}$ and one PEG molecule is covalently attached to Cys$_{46}$-NH$_2$ and wherein each of the PEG molecules has a molecular weight of about 20,000 daltons.

2. The PEGylated GLP-1 compound of claim 1 wherein each of the PEG molecules is a linear methoxy PEG maleimide.

3. A method of treating non-insulin dependent diabetes in a subject in need thereof comprising administering an effective amount of the PEGylated GLP-1 compound of claim 1.

4. A method of treating obesity in a subject in need thereof comprising administering an effective amount of the PEGylated GLP-1 compound of claim 1.

* * * * *